United States Patent [19]

Tantram et al.

[11] Patent Number: 4,829,809
[45] Date of Patent: May 16, 1989

[54] GAS CALIBRATION METHOD AND APPARATUS

[75] Inventors: Anthony D. S. Tantram, Great Bookham; Jonathon H. Gilbey, Maidstone, both of United Kingdom

[73] Assignee: City Technology Limited, United Kingdom

[21] Appl. No.: 79,398

[22] Filed: Jul. 30, 1987

[30] Foreign Application Priority Data

Aug. 26, 1986 [GB] United Kingdom ............. 86 20586
Nov. 11, 1986 [GB] United Kingdom ............. 86 26941

[51] Int. Cl.$^4$ ............................................. G01N 27/30
[52] U.S. Cl. .................................................. 73/23; 422/80
[58] Field of Search ................... 73/23, 27 R; 422/78, 422/80

[56] References Cited

FOREIGN PATENT DOCUMENTS

| 105955 | 6/1985 | Japan | 73/23 |
| 173453 | 9/1985 | Japan | 73/23 |
| 238753 | 11/1985 | Japan | 73/23 |

Primary Examiner—Michael J. Tokar
Assistant Examiner—Joseph W. Roskos
Attorney, Agent, or Firm—Stevens, Davis, Miller & Mosher

[57] ABSTRACT

A gas calibration method providing an absolute standard for the determination of an active gas in a gas mixture, comprises passing the gas mixture into a chamber (1) of known volume. The chamber contains a galvanic sensor (b 2) providing a signal current, proportional to the rate of reaction of the active gas at the sensor electrode, to a current measuring device (8). After sealing the chamber, a signal processing means (9) samples the signals from (8) as a function of time, and calculates the sensitivity of the sensor and the concentration of the active gas.

14 Claims, 1 Drawing Sheet

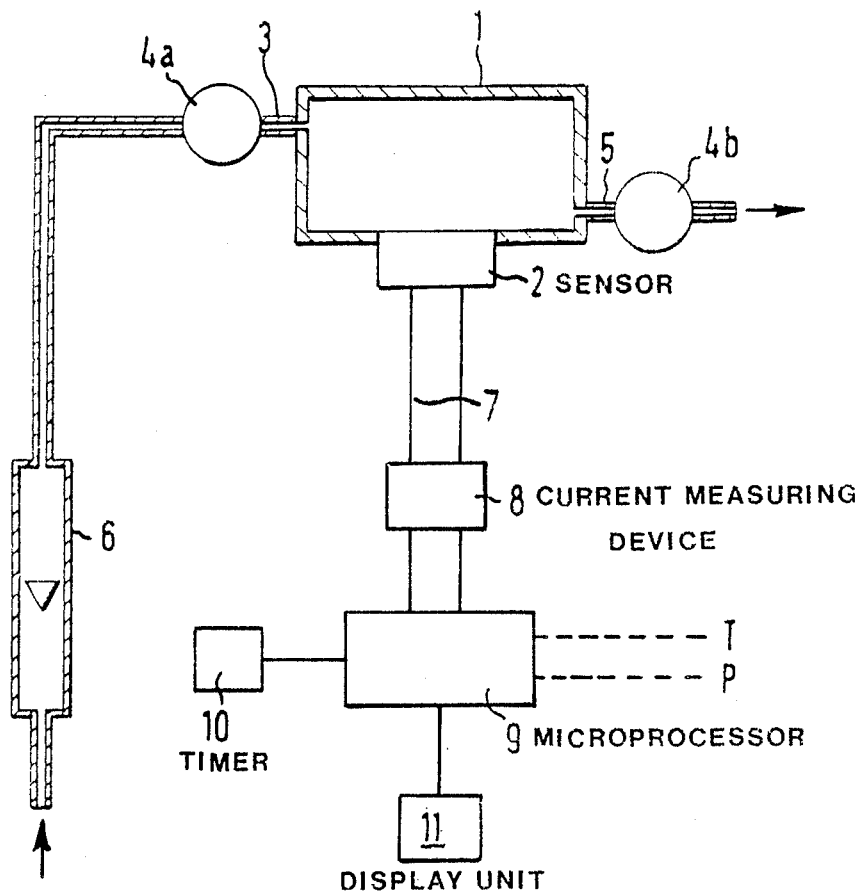

GAS CALIBRATION METHOD AND APPARATUS

This invention concerns a gas calibration method and apparatus; more especially it concerns a method suitable for the calibration of a gas mixture supplied in cylinders by a manufacturer.

Many laboratories or industries use gases for processes or for testing. These gases are geneally purchased in cylinders from a manufacturer at a nominal composition, which is frequently found to be inaccurate. Even when a certificate of analysis is provided, significant discrepancies are often found between different cylinders. This is especially the case where the gas of interest is at a low concentration in a carrier gas and/or where the gas is reactive. Methods exist to give accurate comparative analyses, eg infrared, gas chromatography and electrochemical sensors, but all these instruments themselves require calibration and thus required an absolute or primary standard for this purpose. Chemical analysis is probably the most appropriate method to provide the primary standard, but has the drawbacks that it is a lengthy method and may require such a large amount of gas for accuracy, that the contents of the cylinder may be significantly depleted. Even if an accurate calibration is achieved, the gas composition can change with time, particularly where a reactive component interacts with the cylinder walls or with another component of the gas mixture.

We are aware of the teaching of U.S. Pat. No. 3 857 771, which concerns a portable automated analyser, which in its simplest form has a sample vessel, a sensor means providing a concentration signal, a differentiator circuit deriving from the concentration signal a time rate of change signal, and means for recording the maximum time rate of change signal, the maximum value being proportional to the initial concentration of the component being analysed.

However, a proportional value still requires calibration of the instrument. Furthermore, the specific teaching of this U.S. Patent concerns the analysis of oxygen in liquid systems, particularly for enzyme assays, and could not readily be used for the analysis of gases.

There remains a great need for an analysis method which will provide a primary standard and which is quick and easy to carry out so that it may be used both by the manufacturers of gas mixtues and their customers, and inexpensive apparatus for such a method.

The present invention provides a method for the determination of an active gas in a gas mixture, said method comprising passing said gas mixture into a chamber of known volume containing a galvanic electrochemical sensor capable of producing a current proportional to the rate of reaction of the active gas at the sensor sensing electrode, effectively sealing the chamber at a time zero, recording at least a first and a second current signal from the sensor at first and second times, processing said signals to derive the sensitivity, S, of the sensor to said active gas, and further processing the derived sensitivity and a current signal to derive a value for the concentration of the active gas. The invention also provides an apparatus for carrying out the method of the invention, comprising a chamber of known volume having sealable means for charging and withdrawing a gas sample, and having a galvanic electrochemical sensor having its sensing electrode exposed to the internal volume of the chamber, and means for processing current signals from the sensor at at least first and second times to derive therefrom values for sensor sensitivity and active gas concentration.

A remarkable feature of this invention is that it makes it possible to sample a gas of unknown composition, with an uncalibrated galvanic sensor of unknown sensitivity, and to determine not only the concentration of the gas but also the sensitivity of the sensor.

The invention may be used, in addition to calibrating a source of gas, to monitor an active gas. According to the method of the invention, the sensitivity of the sensor is derived, and thereafter the gas to be monitored is sampled and is passed through the chamber, continuously or intermittently. The previously determined sensitivity of the sensor is used together with the output signal from the sensor to obtain the concentration of the active gas, in known manner.

The invention further includes a gas monitor as described above, which may be self calibrating. Periodically, the chamber is sealed and the method is used to determine, or re-determine, the sensitivity of the sensor. The sensitivity, or up-dated sensitivity, is then used for calculation of the concentration of the active gas when the monitor is in the sampling mode.

Preferably, the sensor is removably mounted in the apparatus, to permit the replacement of an exhausted sensor or replacement of a sensor sensitive to one gas by a sensor sensitive to another gas.

An active gas for the purpose of the present invention is any gas which can be electrochemically oxidized or reduced at the sensing electrode of a galvanic sensor in a definitive manner, that is where the electrochemical reaction is known, specifically the number of electrons involved, and there are no side reactions. The sensor used should produce a current sensibly linear with the concentration of the active gas within the concentration range of interest, ie the % deviation from linearity should be within the desired accuracy of measurement. Suitable sensors are commercially available for such active gases as $O_2$, CO, $H_2$, $H_2S$, $Cl_2$, $SO_2$, NO, $NO_2$, and other gases. It is believed that a sensor having a platinum sensing electrode, especially a platinum black electrode, eg bonded to or deposited on a support such as PTFE, will be suitable for most gases of interest, if biased appropriately. Sensors using other electrocatalysts are available, and may be suitable in particular cases. Most sensors are substantially inert to gases such as $N_2$, Ar, $CH_4$, and the like, but if the gas mixture contains potentially interfering gases, the sensor may be modified as described below.

When measuring other gases in the presence of $O_2$ (eg CO in air), intereference from $O_2$ reduction or water oxidation may be avoided by keeping the sensing electrode potential within appropriate limits as is well known to those skilled in the art. If the gas mixture contains gases for which it is not possible to find specific sensors, then in many cases it will be possible to utilize specific filters which permit the passage of only the gas of immediate interest, to the sensing electrode. Such filters have already been proposed in the art. Usually, however, the gas to be determined in a single gas in a carrier gas such as $N_2$ or air.

Some galvanic sensors may still have a small base line current in the absence of active gas. This may be measured by purging the chamber with pure $N_2$ and then leaving the chamber sealed with a stable base line is recorded. The base line may the be nulled out electronically or may be made an input to a microprocessor which then subtracts this value from subsequently recorded current signals.

The chamber may be purged with the gas mixture under test until a sufficiently constant signal is obtained. The flow of gas may then be terminated and the chamber sealed, when it may be considered to be "time zero". The measurements leading to values for the sensor's sensitivity and the concentration of the active gas may then be commenced.

Suitable chambers for use in the present invention should be substantially inert to the gas mixture concerned and may, for example, be made of materials such as glass or polyvinylidene fluoride polymer.

The volume of the chamber is suitably from 1 cm$^3$ to 200 cm$^3$. It will be understood from the formulae below that the volume of the chamber is significant in that the response time of the system is proportional to the volume and is inversely proportional to the sensitivity of the sensor. Very small volumes may lead to inaccuracies in the measurement of volume and of time. Large volumes may lead to a diffusion gradient within the chamber, resulting in a time lag before the signal processing results in accuracy. The sensitivity of the sensor will affect the time lag. Generally, a less sensitive is preferred to a very sensitive sensor. Preferably, the chamber is cylindrical, and preferably has a height to radius ratio of approximately unity. The chamber volume and geometry, and the sensitivity of the sensor, may be optimized to reduce the influence of any diffusion gradient within the chamber, but it may also be suitable to mount a fan within the chamber in order to thoroughly mix the gas.

The chamber requires means to charge and discharge the gas mixture, and these are suitably inlet and outlet pipes positioned to permit thorough flushing of the chamber. The means must also be effectively sealable, ie the ratio of any loss of active gas to its reaction at the sensing electrode must be sufficiently low not to constitute a significant error factor. Conventional valves, operated manually or remotely, eg solenoid or pneumatic valves operated by a control and/or timer means, may be used. It is also possible to use inlet and outlet capillary tubing of sufficient length that the diffusion rate down the tube is insignificant, in which case the tubing may simply be disconnected rather than being mechanically sealed.

Desirably, the apparatus of the invention includes means for measuring current from the sensor (optionally in the form of a voltage signal), means for measuring time, eg linked to the sealing action, and the processing means. A dedicated microprocessor or a suitably programmed microcomputer may be used as time measuring means and processing means, performing calculations described in more detail below and producing signals representing sensitivity and concentration for display, if desired, on a screen, a print out or on a meter, including LED and LCD numeric displays. The preferred calculations include as terms the gas temperature and pressure, and means are preferably provided to determine these. Suitable sensors may be fitted to the apparatus which produce signals indicative of temperature and pressure and which feed these signals to the processing means, but the temperature and pressure may be established by independent means and fed in manually to the processing means.

The output signal from the sensor will normally be small, eg in the $\mu$A range, and it is preferred to use a first stage amplification circuit before signal processing.

Sensors utilizing a reference electrode are desirably used with a potentiostatic circuit. With small currents, it is important to minimize noise interference, and this is particularly important if only two signals are used for processing. Suitable amplifiers, potentiostat circuits and noise suppression techniques are known to those skilled in the art.

The signal processing may be done in a variety of ways. The basis for the calculation to be performed in Faraday's Law, which states that nF coulombs are produced by the electrochemical reaction of 1 gram mol, where n is the number of electrons involved in the reaction, and F is the Faraday Constant, 96,487 coulombs per gram equivalent. It is thus possible to state that a calculation derived therefrom provides a primary standard.

It has been established that the following laws apply:

$$t = \frac{A}{S} \ln \frac{S^o}{S_t}$$

where t is the time in seconds,
S is the sensitivity of the sensor in uA/unit concentration (concentration units are discussed below)
$S^o$ is the signal $\mu$A at time=0,
$S_t$ is the signal in $\mu$A at time=t, and
A is defined below.

For concentration on a weight per volume basis (g/cm$^3$)

$$A = \frac{VnF \times 10^6}{M}$$

where
M is the molecular weight of the active gas in grams, and
V is the volume of the chamber in cm$^3$.
(In this case the units of sensitivity, S, are $\mu$A per g/cm$^3$.)

For concentrations on a volume per volume basis (parts per million, ppm)

$$A = \frac{VnFP}{6.236 \times 10^4 \, T}$$

where
P is the total pressure in mm Hg, and
T is the temperature in °K.
(In this case the units of sensitivity are $\mu$A per ppm.)

It can be seen that t versus ln $S_t$ will be linear, with a slope of $-A/S$ and an intercept at t=0 of A/S ln $S^o$. The sensitivity can therefore be derived from the slope, the value of $S^o$ from $$\frac{\text{intercept}}{\text{slope}} = \ln S^o$$

and hence the concentration $$C^o = \frac{S^o}{S}.$$

If $S^o$ is derived from the intercept in this manner, rather than being the measured signal at time zero, we believe that any problem of non-linearity because of diffusion resistance within the chamber at time zero, will be substantially avoided.

The calculations may be done manually or by computer or a built-in microprocessor, eg logging and storing successive $S_t$ versus $t$ values, then doing a linear regression on these values to obtain the slope and intercept and finally to comput the sensitivity and concentration.

This sequence may be carried out after a relatively short time, but in general longer times will give more accurate results. Successive computation sequences can be done, effectively updating the initial short time result.

The sensitivity can be calculated from any response of the system and hence the initial concentration calculated from this and the recorded value of $S°$, eg for a 25% response time ($t^{25}$)

$$\frac{S°}{S_t} = \frac{1}{0.75} \text{ and } S = 0.2877 \frac{A}{t} 25$$

and hence the concentration $C° = \frac{S°}{S}$.

More readily, the concentration may also be computed from successive multiples of a given time interval.

If the times selected are $t$ seconds and $bt$ seconds, then $$C° = \left(\frac{S_t}{S_{bt}}\right)\frac{1}{b-1} \times \frac{S_t(b-1)t}{A} \times \frac{1}{\ln\frac{S_t}{S_{bt}}}$$

If the times selected are $t$ with $2t$, $2t$ with $3t$ etc, then $$C° = \frac{S_t}{S_{2t}} \times S_t \times \frac{t}{A} \times \frac{1}{\ln\frac{S_t}{S_{2t}}}$$

$$C° = \left(\frac{S_{2t}}{S_{3t}}\right)^2 \times S_{2t}\frac{t}{A} \times \frac{1}{\ln\frac{S_{2t}}{S_{3t}}}$$

$$C° = \left(\frac{S_{3t}}{S_{4t}}\right)^3 \times S_{3t} \times \frac{t}{A} \times \frac{1}{\ln\frac{S_{3t}}{S_{4t}}}$$

and so on.

One can carry out successive computations, eg either (t, 2t), (2t, 3t) etc. or (t, 2t), (t, 3t) etc., or the value of t may be changed for successive computations.

The invention will now be more particularly described by way of example only, and with reference to the accompanying schematic drawing of an apparatus according to the invention.

A cylindrical chamber 1, of volume of approximately 12 cm$^3$, has fitted in its base a commercial galvanic sensor, 2. A gas supply pipe, 3, fitted with a stopcock, 4a, and a rotary flow meter, 6, connects with the chamber. A gas exit pipe, 5, also fitted with a stopcock, 4b, also connects with the chamber. The sensor has output leads, 7, connected to a current measuring device, 8, which in turn feeds a signal indicative of current to a microprocessor, 9. The microprocessor is also fed with values for temperature and pressure (T and P), either directly from sensors or from a keyboard on which the values are entered manually. A timer, 10, which may form part of the microprocessor internal clock, provides time values to the micrioprocessor. The microprocessor is connected to a display unit, 11.

In operation, the chamber is flushed with nitrogen for 5 to 10 minutes, then sealed off to permit the residual baseline to be recorded as described above, before a supply of a gas mixture is fed through pipe 3 until the microprocessor detects a sufficiently constant current signal. Stopcock 4a, then stopcock 4b, are closed, either manually or automatically under the control of the microprocessor, and the timer is set to zero, again either manually or under software control, and proceeds to count. The microprocessor samples over successive time intervals, and applies a constant regression technique to calculate successive updated values of sensitivity, S, and initial signal, S°, from which it computes values of the gas concentration for display on the display unit.

A test was carried out utilising a mixture of nominally 45.1 ppm CO in $N_2$. this gas mixture had been cross checked against a standard provided by The National Physical Laboratory, Teddington, England, and the resulting confidence level was ±1.5 ppm. The chamber volume was 11.8 cm$^3$. Using programs based on the equations set out above, a microprocessor calculated the following values in successive measurement runs each lasting 10 minutes.

| Regression technique | Two point technique |
| --- | --- |
| 46.2 | 45.9 |
| 45.6 | 45.6 |
| 46.4 | 44.4 |

A further test using the same apparatus was carried out, utilising a mixture of nominally 152 ppm $H_2S$ in $N_2$, stated by the supplier to be within ±3 ppm when the cylinder was originally filled. The CO sensor used in the previous trial was replaced by a commercial $H_2S$ sensor. The following values were obtained in successive runs, each lasting 10 minutes.

| Regression technique | Two point technique |
| --- | --- |
| 149.3 | 151.0 |
| 148.5 | 148.3 |
| 149.4 | 148.3 |
| 149.1 | 148.6 |

Other variations to the method and apparatus of the inventio may be used by the skilled man without departing from the scope of the present invention.

We claim:

1. A method for the determination of an active gas in a gas mixture, comprising passing said gas mixture into a chamber of known volume containing a galvanic electrochemical sensor capable of producing a current proportional to the rate of reaction of the active gas at the sensor's sensing electrode, effectively sealing the chamber at a time zero, recording at least a first and a second current signal from the sensor at first and second times, processing said signals to derive the sensitivity, S, of the sensor to the active gas, and further processing the derived sensitivity and a current signal to derive a value for the concentration of the active gas.

2. A method as claimed in claim 1, wherein the sensor signal at time zero is processed with the derived sensitivity to calculate the concentration of the active gas.

3. A method as claimed in claim 2, wherein the sensor signal is recorded at time zero.

4. A method as claimed in claim 2, wherein the sensor signal at time zero is calculated by extrapolation of a plot of time t against ln $S_t$ to time zero, where $S_t$ is the signal at time t.

5. A method as claimed in claim 1, wherein the signal processing comprises plotting the value of time, t, against ln $S_t$, where $S_t$ is the signal at time t, and deriving the sensitivity of the sensor from the slope of said plot.

6. A method as claimed in claim 1, wherein the signal processing is carried out by a dedicated microprocessor or programmed microcomputer.

7. A method as claimed in claim 6, wherein the signal processing is carried out by a microprocessor which samples the sensor signals over successive time intervals and applies a conventional regression technique to calculate successive updated values of sensor sensitivity and sensor signal at time zero, and computes updated values of the gas concentration for display on a display unit.

8. A method as claimed in claim 7, wherein the microprocessor also samples temperature and pressure transducers to obtain values therefrom, and carries out corrections for sensor sensitivity and gas concentration.

9. An apparatus for determining the concentration of an active gas in a gas mixture, comprising a chamber of known volume containing a galvanic gas sensor capable of producing a current signal proportional to the rate of reaction of said active gas at the sensor's sensing electrode, said sensing electrode being exposed to the internal volume of the chamber, said chamber being provided with sealable means for charging and withdrawing a sample of gas mixture, and means for processing current signals from the sensor at at least first and second times to derive from the signals and time values, a value for sensor sensitivity and active gas concentration.

10. An apparatus as claimed in claim 9, wherein the sensor is removably mounted in the chamber.

11. An apparatus as claimed in claim 9, wherein the volume of the chamber is from 1 to 200 $cm^3$.

12. An apparatus as claimed in claim 9, wherein the chamber is substantially cylindrical and has a height to radius ratio of approximately unity.

13. An apparatus as claimed in claim 9, wherein the sealable means are inlet and outlet capillary tubes, and effective sealing is obtainable by disconnection of the inlet tubes from the supply of gas mixture.

14. An apparatus as claimed in claim 9, wherein the means for processing is a dedicated microprocessor or a programmed microcomputer.

* * * * *